United States Patent [19]

König et al.

[11] Patent Number: 4,990,447

[45] Date of Patent: Feb. 5, 1991

[54] PROCESS FOR THE PURIFICATION OF SERUM ALBUMIN

[75] Inventors: Boudewijn W. König; Michiel N. Hamers, both of Amsterdam; Cornelis J. van der Laken, Leiden, all of Netherlands

[73] Assignee: Gist-Brocades NV, Delft, Netherlands

[21] Appl. No.: 317,818

[22] Filed: Mar. 1, 1989

Related U.S. Application Data

[63] Continuation-in-part of Ser. No. 210,824, Jun. 24, 1988, abandoned.

[51] Int. Cl.$^5$ .......................... C07K 3/28; C12N 15/14
[52] U.S. Cl. .................................. 435/71.1; 435/71.2; 530/364; 935/11; 935/12
[58] Field of Search .............. 530/364; 435/71.1, 71.2; 935/11, 12

[56] References Cited

U.S. PATENT DOCUMENTS 4,086,222  4/1978  Lindquist et al. ................ 530/364
4,228,154  10/1980  Fisher et al. .................. 530/364 X

FOREIGN PATENT DOCUMENTS 0073646  3/1983  European Pat. Off. .
2327256  6/1977  France .
1471006  4/1977  United Kingdom .

OTHER PUBLICATIONS

Chem. Abstracts, 91:119043k, 1979 (Hori).
Biochimica et Biophysica Acta 372: 218–224 (1974), Wichman et al.

Primary Examiner—Howard E. Schain
Attorney, Agent, or Firm—Barbara Rae-Venter

[57] ABSTRACT

Recombinantly produced serum albumin is purified in a series of steps, initially employing an alkaline precipitation, optionally followed by incubation with an anion exchange absorbent, followed by affinity chromatography employing a hydrophobic solid phase and using a water-soluble lipid anion as desorbens in the aqueous phase.

25 Claims, 8 Drawing Sheets

PROCESS FOR THE PURIFICATION OF SERUM ALBUMIN

This application is a continuation-in-part of U.S. patent application Ser. No. 210,824 filed June 24, 1988, now abandoned.

TECHNICAL FIELD

The field concerns purification of recombinantly produced proteins, particularly serum albumin.

BACKGROUND AND RELEVANT LITERATURE

Human serum albumin ("HSA") is the major protein component of plasma and consists of a single polypeptide chain of 585 amino acids, having a molecular weight of about 66,000 daltons. Its 17 intramolecular disulfide bridges contribute to the high stability of the albumin molecule.

The primary function of albumin in plasma is maintenance of the colloid osmotic pressure within the blood vessel. Furthermore, the protein acts as a carrier of several ligands, for instance bilirubin and fatty acids. (See reviews by F. Rothstein, V. M. Rosenoer and W. L. Hughes, in *Albumin Struct. Funct. Uses* (1977) 7-25; U. Kragh-Hansen, *Pharmacol. Rev.* (1981) 33:17-53; T. Peters Jr., in *Adv. Prot. Chem.* (1985) 37:161-245.)

Purified serum albumin is indicated for the prevention and treatment of hypovolemic shock, in conditions where there is severe hypoalbuminemia, as an adjunct in hemodialysis and in cardiopulmonary bypass procedures and in conjunction with exchange transfusion in the treatment of neonatal hyperbilirubinemia.

For the large scale purification of HSA from plasma or placenta, precipitation methods using ethanol, polyethyleneglycol, trichloroacetic acid or ammonium sulphate together with Rivanol ® and/or liquid chromatography methods are frequently applied. (See for the latter, J. Saint-Blancard, J. M. Kirzin, P. Riberon, F. Petit, J. Fourcart, P. Girot and E. Boschetti, *Anal. Chem. Symp. Ser.* (1982) 9:305-312; J. M. Curling, in *Methods of Plasma Protein Fractionation* (1980) 77-91; M. J. Harvey, in *Methods of Plasma Protein Fractionation* (1980) 189-200; N. E. Schultze and J. F. Heremans, *Mol. Biol. Hum. Prot.* (1966) 1:261-270; J. Liautau, J. Pla, A. Debrus, P. Gattel, R. Plan and L. Peyron, 13 th Int. Congr. IABS (1973) 27:107-114; Hao, Y-L, *Vox Sang* (1985) 49:1-8; and U.S. Pat. No. 4,228,154.)

On a laboratory scale the application of affinity chromatography for the purification of serum albumin has been described by T. Peters Jr., H. Taniuchi and C.B. Anfinsen Jr., in *J. Biol. Chem.* (1973) 248(7):2447-2451; A. Wichman and L-O. Andersson, *Biochim. Biophys. Acta* (1974) 372:218-224; and A. Aslam, D.J. Jones and T.R. Brown, *Anal. Biochem.* (1976) 75:329-335.

Since large amounts of serum albumin are necessary for therapy and the source of serum albumin (plasma) is limited, other techniques have been sought to produce HSA in large quantities. Successes have been reported in the production of HSA by fermentation using transformed microorganisms or cell lines made by recombinant DNA techniques. See, for example, EP-A-0073646.

However, one of the major problems in the purification of serum albumin produced by fermentation using transformed cells is the presence of contaminating components from the growth medium (fermentation broth) or cell lysate, which have to be removed in order to obtain purified, homogeneous serum albumin.

These contaminants are for example foreign proteins which would be expected to produce an immunological response. Administration of contaminated HSA could lead to shock. These contaminants are totally different from those which occur during fractionation of the serum albumin from plasma or placenta. This means that the purification methods developed for HSA from natural sources cannot be extrapolated to the purification of recombinant serum albumin. Practical processes for large scale purification of human serum albumin produced by transformed microorganisms or cell lines have not been published so far and are not yet available.

SUMMARY OF THE INVENTION

Recombinantly produced serum albumin is purified by an initial stage of alkaline precipitation, optionally ion exchange chromatography at an acidic pH, and affinity chromatography employing a lipophilic surface immobile phase using a lipid anion as desorbens in the aqueous phase. High recoveries and purities are achieved.

DESCRIPTION OF THE SPECIFIC EMBODIMENTS

Figure 1:
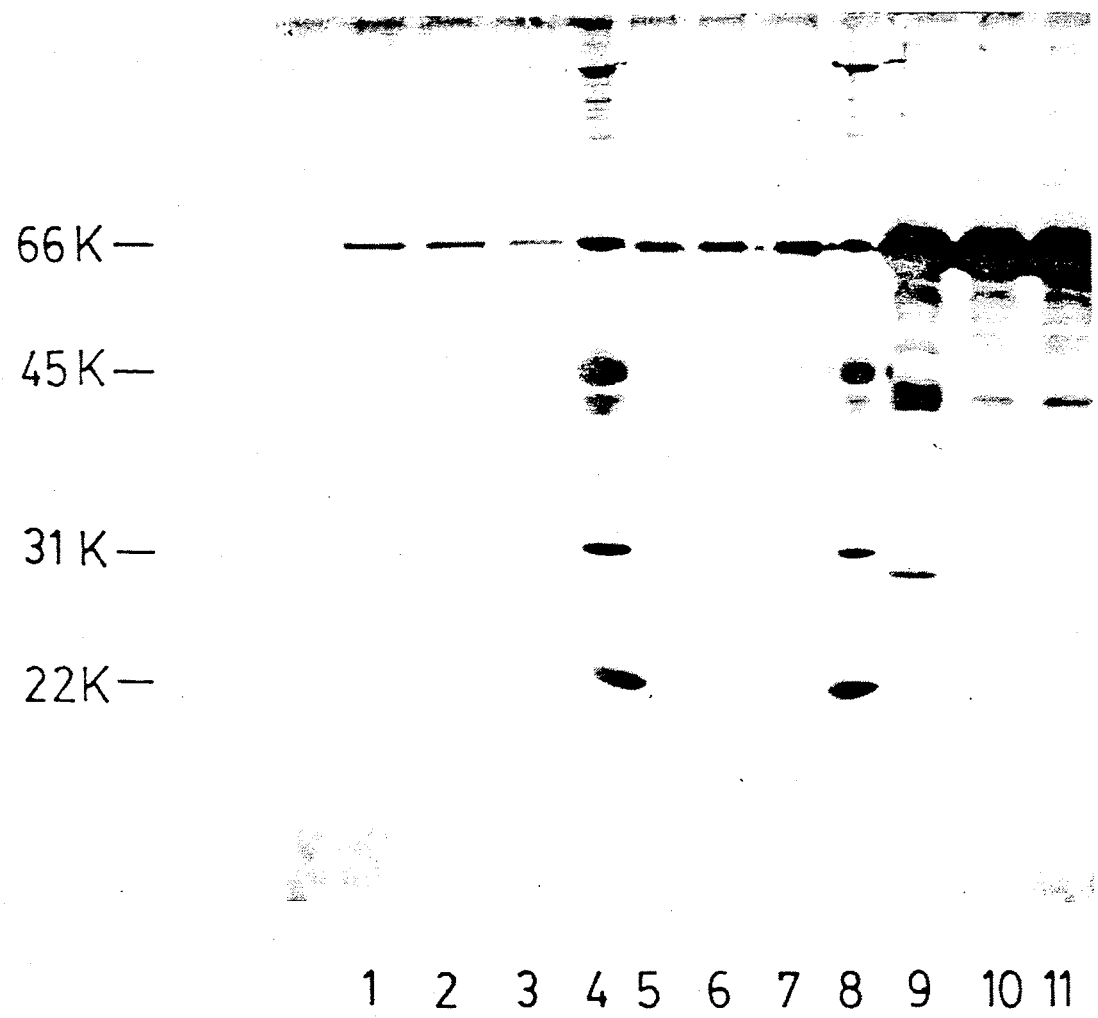
FIG. 1: SDS-PAGE of human serum albumin under reducing conditions (silver-stain). Defatted HSA: lanes 1 (100 ng); 5 (500 ng); 9 (10 µg). Purified HSA: lanes 2,3 (100 ng); 6,7 (500 ng); 10,11 (10 µg). Molecular weight markers: lanes 4,8.

In accordance with the subject invention, serum albumin, particularly human serum albumin, prepared by recombinant techniques, is purified with high recovery and in high purity for use as a pharmacological product.

The purification method is preceded by filtration of a fermentation broth. The method can be applied to the thus obtained supernatant or to the cells after lysis. It generally involves alkaline precipitation of contaminants; optionally treatment with an acidic anion exchange resin and optionally dialysis to concentrate the medium, followed by affinity chromatography employing a lipophilic immobile phase and a lipophilic anion as desorbens in the eluens. The serum albumin may then be harvested by desalting and concentration. If desired, the serum albumin may be lyophilized to provide for a dry product.

The serum albumin produced by the subject process is substantially homogeneous and monomeric as determined by ion exchange chromatography, size exclusion chromatography, SDS-PAGE and immunological testing involving immunization of rabbits.

The method finds use with the production of serum albumin, particularly human serum albumin, prepared by recombinant techniques employing microorganisms. The microorganisms may be prokaryotic or eukaryotic, particularly eukaryotic, and include bacteria such as *E. coli, B. subtilis, B. licheniformis, Streptomyces, Pseudomonas*, etc. Among eukaryotes are yeasts, such as *Saccharomyces, Schizosaccharomyces, Kluyveromyces, Candida* etc., filamentous fungi, *Neurospora, Aspergillus*, etc.

The expression of the serum albumin may result in secretion or retention of the product in the organism. The broth may be removed batch-wise or continuously from the fermenter. In the case of secretion, the cell-free supernatant is used in the purification process. The cell-free supernatant is obtained by clarification of the fermentation broth, conveniently by centrifuging or filtering the broth, using ultrafiltration for concentration of the protein product. The filter will generally have a cut-off of 500–25,000, more usually at least about 1000D. Desirably, the final product concentration should be at least about 0.5 mg/ml, preferably at least about 1 mg/ml. Where the product is retained in the cytoplasm of the cell, the cells are harvested. A lysate may be produced in accordance with any convenient technique, using mechanical or chemical disruption of the cells to produce the lysate. The cellular debris may be removed by centrifugation.

The pH of the cell-free supernatant or cell lysate is adjusted to about 7.5 to 9, more preferably 8 to 8.5. The pH may be modified by any convenient means, such as the addition of sodium hydroxide, or other convenient base, usually at a normality in the range of about 0.1 to concentrated. The mixture is conveniently stirred for a short time, generally for about 5 to 30 min and filtered through a filter which substantially retains particles of greater than about 25 μ, preferably greater than about 20 μ, more preferably greater than about 5 μ. The precipitate is washed with an appropriately buffered solution, usually buffered at a pH below 8, generally dilute, where the buffer concentration will be from about 20 to 100 mM. Desirably, the buffer will be at a pH in the range of about pH 6.5 to 8. The volume of the washes is not critical, generally being from about 0.1 to 0.5, based on the volume of the filtrate. The buffer will generally have a conductivity of about 0.1 to 100 mS/cm, preferably between about 1 to 50 mS/cm. Afterwards, the filtrate and washes are combined.

The next essential step is affinity chromatography, where a lipophilic immobile phase is used. In the affinity chromatography step, the serum albumin containing solution is contacted with a solid surface, usually particles in a column, which are coated with or functionalized with lipophilic chains of about 6 to 12 carbon atoms, preferably from about 6 to 10 carbon atoms, more preferably 8 carbon atoms, where the group will normally include an alkyl group bonded to a functionality for covalent bonding to the support. Illustrative compounds include octanoate, octylsuccinate, etc., where the lipophilic group may be bonded to the support through an ether, amide, or other stable functionality. Included in the eluens will be a lipophilic compound, conveniently a carboxylate, ester, or the like which is soluble in the aqueous medium at a concentration in the range of about 50 to 250, more usually 75 to 150 mM. For further description of the technique, see Wichman and Andersson (1974), supra.

In carrying out the affinity chromatography, the medium will be at about physiologic pH, normally in the range of about 6.5 to 8, more usually in the range of about 7 to 7.5. The buffer concentration will generally be in the range of about 50 to 150 mM.

Desirably, at the loading of the serum albumin medium onto the affinity adsorbent, the column is washed with the equilibration buffer to which about 0.5–1.5 M salt (NaCl) is added.

Desirably, either prior to or subsequent to the affinity chromatography, ion exchange is also used to further enhance the purification of the serum albumin. In the former case, the precipitate is washed with a buffered solution, usually buffered at a pH below 7, generally dilute, where the buffer concentration will be from about 20 to 100 mM. Desirably, the buffer will be at a pH in the range of about pH 4 to 5.5. The volume of the washes is not critical, generally being from about 0.1 to 0.5, based on the volume of the filtrate. The buffer will generally have a conductivity of about 0.1 to 100 mS/cm, preferably between about 1 to 50 mS/cm. After combining the filtrate and washes, the pH of the solution is lowered to about pH 3.5 to 6, preferably 4 to 5.5. In the latter case, subsequent to the affinity chromatography, the pH of the eluate is lowered to about pH 3.5 to 6, preferably 4 to 5.5.

The ion exchange step aids in removing nucleic acids, contaminating proteins and pigments. The serum albumin medium may be combined with the ion exchange resin either batch-wise or continuously through a column, where contact will normally be maintained for from about 5–60 min, preferably 10–30 min. An anion exchange adsorbent is employed, such as QAE, or DEAE bound to a commercially available carrier. The serum albumin medium will be employed as an acidic medium, generally having a pH in the range of 3.5 to 6, more usually in the range of about 4 to 5.5, which may be readily achieved by the addition of a variety of acids or buffers. The buffer concentration will generally be in the range of about 25 to 100 mM. The weight ratio of ion exchange resin to protein will generally be at least about 1:1 and not exceed about 30:1, preferably being about 5–15:1, more preferably about 10:1. Prior to use, the anion exchange resin will normally be equilibrated with the low pH buffer employed with the serum albumin medium.

The serum albumin medium is then isolated from the resin by any convenient means, e.g. centrifugation for 5 min, 2000×g, followed by washing the ion exchange resin with the low pH buffer, where the volume of the low pH buffer to volume of the ion exchange resin will generally be about 1 to 20 times, usually 2 to 10 times. One or more washings may be used, usually two. The liquid media are combined and the pH will normally be raised to about neutral, generally in the range of about 6.5 to 8, more usually about 7 to 8. The approximately neutral medium is then dialyzed against, for instance, a phosphate buffer with a pH of about 6-10, preferably about 6-8, with a conductivity of about 0.5 to 100 mS/cm, preferably about 0.5 to 20 mS/cm. In any case, the buffer solution will be the same as that used in the affinity column. Concentration of the medium will usually afford a concentrate of about 1 to 20 mg protein/ml, more usually about 2 to 15 mg/ml.

A wide variety of supports and adsorbents may be used as the solid carriers or supports. Such solid carriers include inorganic carriers, such as glass and silica gel, organic, synthetic or naturally-occurring carriers, such as agarose, cellulose, dextran, polyamide, polyacrylamides, vinyl copolymers of bifunctional acrylates, and various hydroxylated monomers, and the like. Commercially available carriers are sold under the names of Sephadex®, Trisacryl®, Ultrogel®, Dynospheres®, Macrosorb®, XAD resins, and others.

The conditions for the various steps will be carried out at non-denaturing conditions, generally at convenient temperatures in the range of about $-10°$ C. to $+30°$ C., more usually at about ambient temperatures. The chromatographic steps may be performed batchwise or continuously, as convenient. Any convenient method of separation may be employed, such as centrifugation, filtration, decanting, or the like.

A preferred embodiment of the invention comprises:
growing in a nutrient medium yeast cells transformed with an expression construct comprising a structural gene encoding serum albumin, wherein serum albumin is expressed;
isolating a product medium as clarified fermentation broth or cell lysate;
making the product medium alkaline to a pH in the range of about 7.5 to 9 and separating the alkaline medium from the precipitate;
acidifying said alkaline medium to a pH in the range of about 4.0 to 5.5 and incubating said acidified medium with an anion exchange adsorbent;
changing the pH of said acidified medium to about physiologic pH to provide a concentrated serum albumin and chromatographing said concentrated medium with a lipophilic immobile phase and eluting the albumin by adding as desorbens a water soluble lipid anion; and
isolating purified serum albumin substantially free of contaminants from said microorganism.

The following examples are offered by way of illustration and not by way of limitation.

EXPERIMENTAL

Example 1

Purification of HSA from a Clarified Fermentation Broth

The *Kluyveromyces lactis* strain CBS 2360 was grown for 70 hours at 30° C. in a medium containing yeast extract, 0.5% (w/v), corn steep solids, 2% (w/v), glucose, 0.7% (w/v) and mineral salts. During the fermentation glucose was fed. The fermentation broth was centrifuged (5 min at 4000 rpm) and the supernatant was filtered through a Seitz K 500 filter. The final solution was concentrated 6 times by ultrafiltration using a filter with a cut-off of 1000 D. The final protein concentration was 1 mg/ml.

Alkaline precipitation. To this clarified concentrated fermentation broth, defatted purified HSA (Cohn Fraction V) was added so that the content of HSA was 90% (w/w) of the protein content (10 mg/ml). The pH of the HSA-containing solution was increased to pH 8.1, stirred for 15 min and filtered through a 20 μm filter. The filtercake was washed twice with 50 mM sodium acetate pH 4.5 and subsequently the pH of the combined filtrates was adjusted to pH 4.5.

QAE-Sephadex chromatography. The HSA solution obtained in the previous step was incubated batch-wise for 30 min with QAE-Sephadex A-50®, which had been equilibrated with 50 mM sodium acetate buffer pH 4.5, at a ratio (w/w) of protein:adsorbent (dry weight) of 1:10. After incubation, the gel suspension was removed by centrifugation and subsequently washed twice with 50 mM sodium acetate buffer pH 4.5. The collected supernatants were combined and the pH of this solution was adjusted to pH 7.4 and subsequently dialyzed and concentrated to a protein concentration of 10 mg/ml.

Affinity chromatography. The HSA solution obtained in the previous step was contacted with octylsuccinate anhydride coupled to 1,4-diaminobutane Sepharose 4B according to A. Wichman and L-O. Andersson (1974) supra. This affinity adsorbent was equilibrated with 100 mM sodium phosphate buffer pH 7.4. After loading of the HSA-containing solution onto the affinity adsorbent and washing it with the equilibration buffer to which 1 M NaCl had been added, elution of HSA was carried out with 100 mM sodium phosphate buffer (pH 7.4) to which 100 mM sodium octanoate had been added. The purified HSA was desalted and concentrated to a protein concentration of 10 mg/ml.

Figure 2:
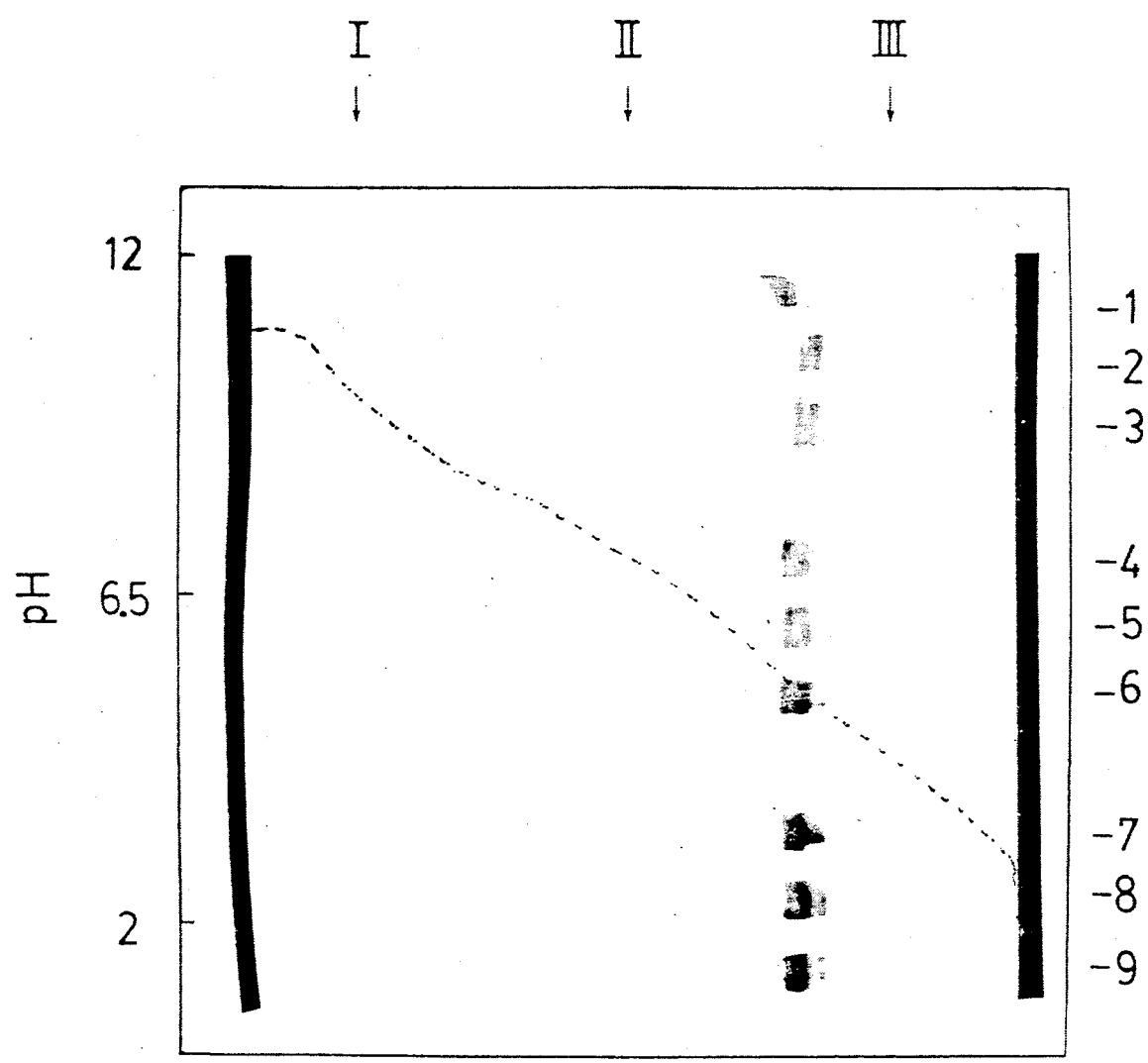
FIG. 2: Isoelectrofocusing of human serum albumin (CBB R-250 stain). I: point of application for samples in lanes 1,2,3. II: point of application for samples in lanes 4,5,6. III: point of application for samples in lanes 7,8,9. Defatted HSA (10 µg): lanes 1,4,7. Purified HSA (10 µg): remaining lanes.
Figure 3:
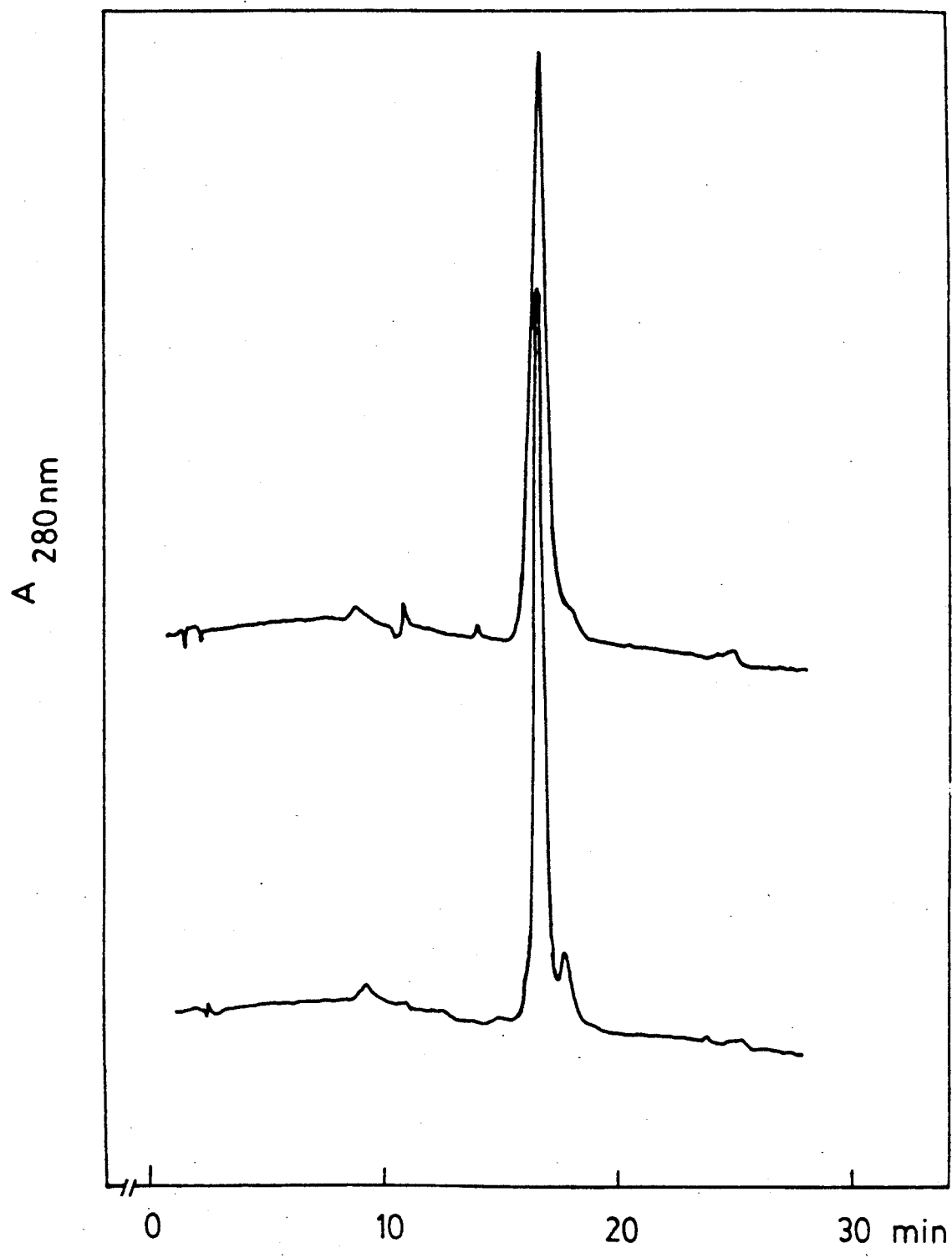
FIG. 3: High performance ion exchange chromatography of human serum albumin on Mono Q ®. Upper chromatogram: purified HSA; lower chromatogram: defatted HSA.
Figure 4:
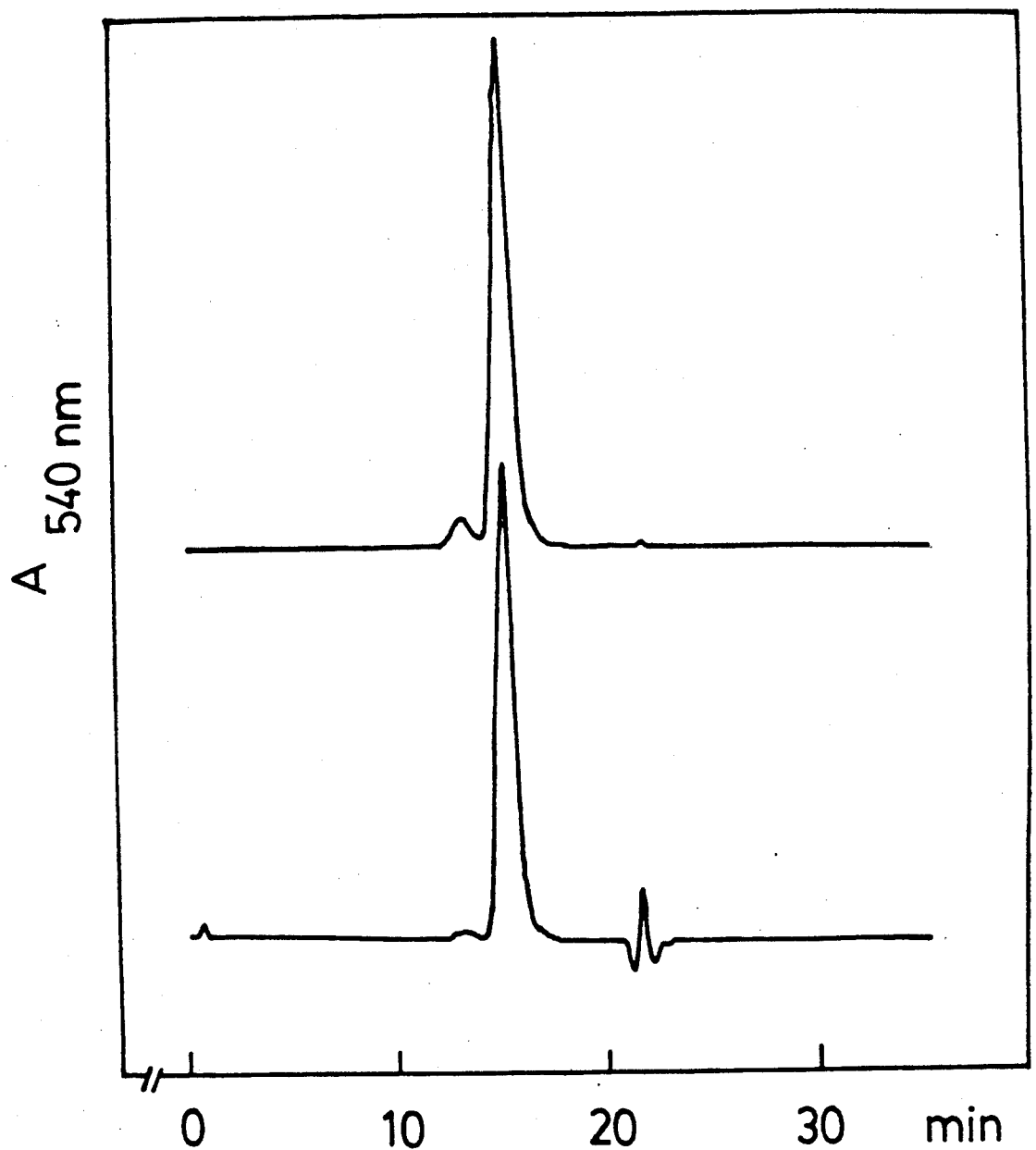
FIG. 4: High performance size exclusion chromatography of human serum albumin on Bio-Sil TSK-250 ®. Detection of protein by post-column derivatization with a protein reagent. Upper chromatogram: defatted HSA; lower chromatogram: purified HSA.

Following the procedure described in this example the recovery of HSA was 75% and no contaminants could be demonstrated by SDS-PAGE (FIG. 1), IEF (FIG. 2), HPIEC (FIG. 3) and HPSEC (FIG. 4), which results are indicative of the high purity of the obtained HSA.

Furthermore, characterization of purified serum albumin was also performed by immunological methods: rabbits were immunized with the purified HSA and the antisera were screened for antibody response against defatted HSA or *Kluyveromyces lactis* proteins from the fermentation broth according to the double diffusion method of O. Ouchterlony, *Acta Path. Microbiol. Scand.* (1948) 28:186-191. Using this technique only antibodies directed towards HSA were detected.

Example 2

Figure 5:
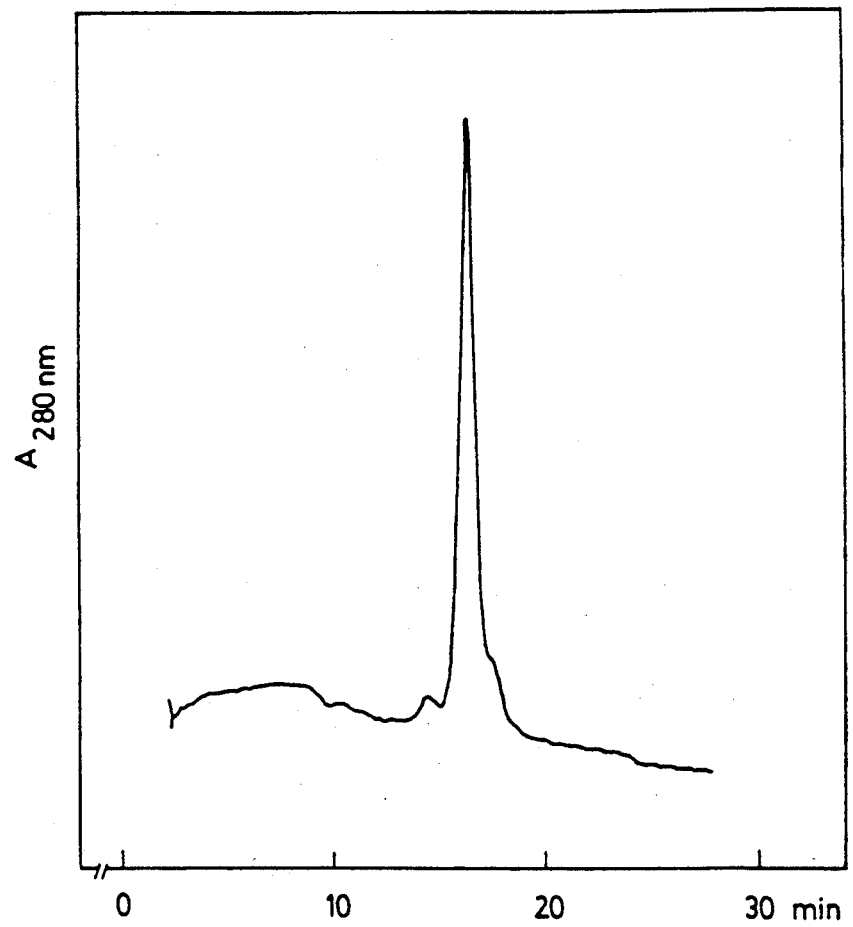
FIG. 5: High performance ion exchange chromatography on Mono Q ® of human serum albumin purified with alkaline precipitation and affinity chromatography.

Purification of HSA from a Clarified Fermentation Broth without Ion Exchange Chromatography Example 1 was repeated but without the ion exchange step. The HSA recovery (90%) of this process was higher than the one obtained in Example 1. Although the ratio albumin to protein (w/w) was 1, the HPIEC chromatogram of the purified serum albumin (FIG. 5) revealed a small peak in front of the HSA peak. Besides, in contrast to defatted HSA and the HSA obtained in Example 1, the final product was faintly yellow-coloured which indicates the presence of a pigment originating from the fermentation broth.

Example 3

Purification of HSA from a Clarified Cell Lysate

The cell paste of *Kluyveromyces lactis* (CBS 2360; cultured as described in Example 1) was 1:1 diluted with water and disrupted by glass beads in a Dynomill apparatus. The lysed cells were centrifuged for 20 min at 15,000 rpm in a Sorvall centrifuge, SA 600 rotor and the supernatant was used as such.

Alkaline precipitation. To the clarified cell lysate, defatted purified HSA (Cohn Fraction V) was added so that the content of HSA was 5% (w/w) of the total protein content: 10 mg/ml. The pH of the HSA-containing solution was increased to pH 8.1, stirred for 15 min and filtered through a 20 μm and 5 μm filter. The filtercake was washed twice with 50 mM sodium acetate buffer pH 4.5 and subsequently, the pH of the combined filtrates was adjusted to pH 4.5.

QAE-Sephadex chromatography. The HSA solution obtained in the previous step was batch-wise incubated with QAE-Sephadex A-50 ® (ratio (w/w) adsorbent:-protein=10:1), which had been equilibrated with 50 mM sodium acetate buffer pH 5.0, containing 0.25 M NaCl. After incubation, the gel suspension was removed by centrifugation and the adsorbent washed twice with the equilibration buffer.

The collected supernatants were combined, the pH of this solution was adjusted to 7.4 and subsequently the HSA-containing solution was dialyzed and concentrated to a protein concentration of 10 mg/ml. Further processing of the impure solution, containing HSA, was carried out by affinity chromatography as described in Example 1. The HSA recovery was 50% and the purity of the final product, specified as mg albumin/mg protein was 0.85.

Example 4

Purification of recombinant HSA from a Clarified Fermentation Broth

The *Kluyveromyces lactis* strain CBS 2360, transformed with a plasmid containing the gene for HSA as described in Example 10 of the non-prepublished EP-A-88201632.2 (filed July 28, 1988), was grown for 110 hrs at 30° C. in a medium as described in Example 1 of the present specification. During the fermentation glucose was fed. The fermentation broth was centrifuged (5 min at 4000 rpm) and the supernatant was concentrated 20 times by ultrafiltration using a filter with a cut-off of 1000 D. The final protein concentration was 10 mg/ml of which 0.45 mg/ml consisted of monomeric HSA produced with recombinant technques.

The pH of the recombinant HSA-containing solution was increased to pH 8.1. The solution was stirred for 15 min and filtered through a 20 μm filter. The filtercake was washed twice with 50 mM sodium acetate pH 4.5 and subsequently the pH of the combined filtrates was adjusted to 4.5. Further purification of recombinant HSA using QAE-Sephadex chromatography and affinity chromatography was performed as described in Example 1.

Figure 6:
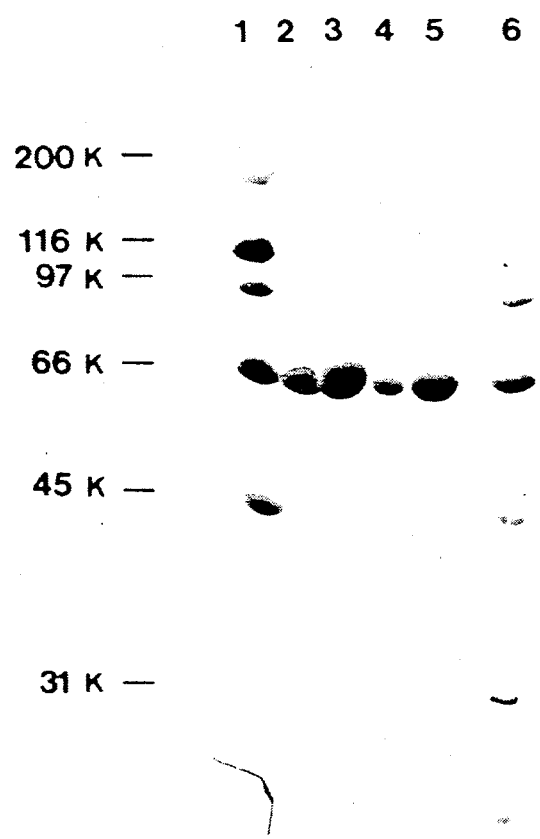
FIG. 6: SDS-PAGE of human serum albumin under reducing conditions (CBB R-250 stain). Defatted HSA: lanes 2 (50 µg) and 3 (100 µg). Purified recombinant HSA: lanes 4 (35 µg) and 5 (70 µg). Molecular weight markers lanes 1 and 6 (20 µg).
Figure 7:
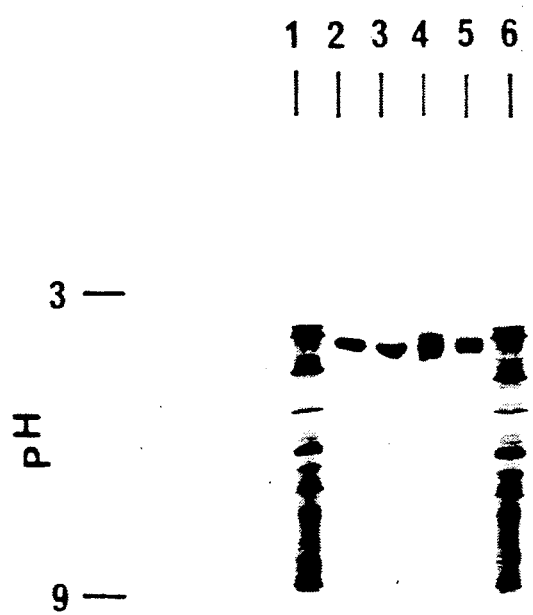
FIG. 7: Isoelectrofocussing of human serum albumin (Ag-stain). Markers: lanes 1 and 6. Defatted HSA: lanes 2 (0.25 µg) and 3 (0.50 µg). Purified recombinant albumin: lanes 4 (0.50 µg) and 5 (0.25 µg).
Figure 8:
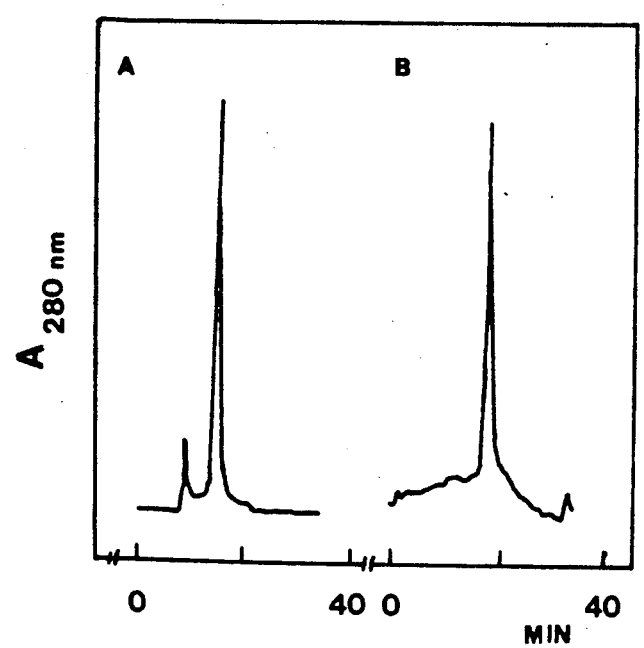
FIG. 8: High performance liquid chromatography of recombinant HSA. HPSEC on Bio-Sil TSK-250 ® (A), HPIEC on Mono Q ® (B).

Following the procedure described in this Example, the recovery of the purified monomeric recombinant albumin, which is faintly yellow-coloured, was 70%. Minor contaminants (in total <8%) could be demonstrated by SDS-PAGE (FIG. 6), IEF (FIG. 7), HPSEC (FIG. 8A) and HPIEC (FIG. 8B).

It is evident from the above results, that the subject invention provides for a rapid and efficient purification of serum albumin made using recombinant techniques. Thus, a rapid and efficient process is provided for purifying serum albumin and similar proteins to provide a product substantially free of contamination from the microorganisms employed as the expression hosts. In this way, products can be obtained which are useful for pharmaceuticals, may be produced efficiently in large quantities, and be obtained at high levels of recovery.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for producing purified recombinant serum albumin at least substantially free of contaminants from a host microorganism comprising:
   growing in a medium microorganisms transformed with an expression construct comprising a structural gene encoding serum albumin, whereby serum albumin is expressed;
   isolating a product medium as a clarified fermentation broth or cell lysate;
   making the product medium alkaline to produce a precipitate without the addition of additional agents and separating, said alkaline medium from said precipitate;
   changing the pH of said alkaline medium to about physiologic pH to provide an aqueous phase comprising concentrated serum albumin and chromatographing said aqueous phase with a lipophilic immobile phase and eluting the albumin by adding as desorbens a water soluble lipid anion to said aqueous phase; and
   isolating purified serum albumin at least substantially free of contaminants from said microorganism.

2. A method according to claim 1, said method further comprising prior to said chromatographing, acidifying said alkaline medium and incubating the resulting acidified medium with an anion exchange resin.

3. A method according to claim 2, wherein said acidified medium is at a pH in the range of 4.0 to 5.5.

4. A method according to claim 2, including the additional step of dialyzing said acidified medium after said incubation.

5. A method according to claim 3, including the additional step of dialyzing said acidified medium after said incubation.

6. A method according to claim 1, wherein said alkaline medium is at a pH in the range of about 7.5–9.0.

7. A method according to claim 2, wherein said alkaline medium is at a pH in the range of about 7.5–9.0.

8. A method according to claim 4, wherein said alkaline medium is at a pH in the range of about 7.5–9.0.

9. A method according to claim 1, wherein said desorbens has an alkyl group of from about 6 to 12 carbon atoms.

10. A method according to claim 2, wherein said desorbens has an alkyl group of from about 6 to 12 carbon atoms.

11. A method according to claim 4, wherein said desorbens has an alkyl group of from about 6 to 12 carbon atoms.

12. A method according to claim 9, wherein said desorbens is a carboxylate of from about 6 to 12 carbon atoms.

13. A method according to claim 1, wherein said desorbens is a carboxylate of from about 6 to 12 carbon atoms.

14. A method according to claim 1, including the additional step of dialyzing said purified serum albumin.

15. A method according to claim 2, including the additional step of dialyzing said purified serum albumin.

16. A method according to claim 4, including the additional step of dialyzing said purified serum albumin.

17. A method according to claim 1, wherein said microorganism is a yeast.

18. A method according to claim 2, wherein said microorganism is a yeast.

19. A method according to claim 4, wherein said microorganism is a yeast.

20. A method according to claim 14, wherein said microorganism is a yeast.

21. A method according to claim 1, wherein said serum albumin is human serum albumin.

22. A method according to claim 2, wherein said serum albumin is human serum albumin.

23. A method according to claim 4, wherein said serum albumin is human serum albumin.

24. A method according to claim 14, wherein said serum albumin is human serum albumin.

25. A method according to claim 17, wherein said serum albumin is human serum albumin.

* * * * *